United States Patent
Suzuki et al.

(10) Patent No.: US 8,062,492 B2
(45) Date of Patent: Nov. 22, 2011

(54) METHOD FOR ANALYZING PROTEIN

(75) Inventors: Yoshio Suzuki, Ibaraki (JP); Kenji Yokoyama, Ibaraki (JP); Ichiji Namatame, Tokyo (JP)

(73) Assignees: National Institute of Advanced Industrial Science and Technology, Tokyo (JP); Sharp Kabushiki Kaisha, Osaka-shi (JP); Toppan Printing Co., Ltd, Tokyo (JP); Katayanagi Institute, Hachioji-shi (JP)

( * ) Notice: Subject to any disclaimer, the term of this patent is extended or adjusted under 35 U.S.C. 154(b) by 764 days.

(21) Appl. No.: 12/090,789

(22) PCT Filed: Oct. 18, 2006

(86) PCT No.: PCT/JP2006/321197
§ 371 (c)(1), (2), (4) Date: Apr. 18, 2008

(87) PCT Pub. No.: WO2007/046537
PCT Pub. Date: Apr. 26, 2007

(65) Prior Publication Data
US 2009/0045060 A1 Feb. 19, 2009

(30) Foreign Application Priority Data
Oct. 19, 2005 (JP) ................ 2005-304478

(51) Int. Cl.
*G01N 27/447* (2006.01)
*G01N 27/453* (2006.01)

(52) U.S. Cl. ................ 204/600; 204/450

(58) Field of Classification Search ............ 204/450, 204/463, 600; 436/512, 516
See application file for complete search history.

(56) References Cited

U.S. PATENT DOCUMENTS
4,886,744 A * 12/1989 Arnost et al. .............. 435/6
5,616,502 A * 4/1997 Haugland et al. ........... 436/86

FOREIGN PATENT DOCUMENTS
JP 62 502548 10/1987
JP 2004 317297 11/2004

OTHER PUBLICATIONS

Suzuki et al., Design and Synthesis of Intramolecular Charge Transfer-Based Fluorescent Reagents for the Highly-Sensitive Detection of Proteins, JACS, 2005,127, 17799-17802.*

Suzuki, Yoshio et al., "Design and Synthesis of Intramolecular Charge Transfer-Based Fluorescent Reagents for the Highly-Sensitive Detection of Proteins", Journal of the American Chemical Society, vol. 127, No. 50, pp. 17799-17802, (2005).

* cited by examiner

*Primary Examiner* — Alex Noguerola
*Assistant Examiner* — Gurpreet Kaur
(74) *Attorney, Agent, or Firm* — Oblon, Spivak, McClelland, Maier & Neustadt, L.L.P.

(57) ABSTRACT

A method for analyzing proteins with the use of electrophoresis is provided, which makes it possible to rapidly and conveniently analyze a great variety of proteins with high sensitivity. The method for analyzing a protein in a sample comprises setting a sample in a carrier for electrophoresis, performing electrophoresis for the sample using a buffer for electrophoresis in which a labeling compound represented by formula I:

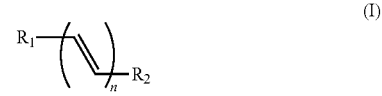

(I)

wherein $R_1$ is an aryl group or a heteroaryl group that may be substituted, $R_2$ is a heterocyclic group that may be substituted, and n is an integer between 1 and 5, is dissolved, and then detecting a complex of the compound of formula I and the protein via spectrophotometrical measurement.

8 Claims, 3 Drawing Sheets

METHOD FOR ANALYZING PROTEIN

CROSS-REFERENCE TO RELATED APPLICATIONS

This application is a 371 of PCT/JP06/321197 filed Oct. 18, 2006 and claims the benefit of JP 2005-304478 filed Oct. 19, 2005.

TECHNICAL FIELD

The present invention relates to a method for efficiently detecting, qualitatively analyzing, or quantitatively analyzing proteins by electrophoresis.

BACKGROUND ART

Proteome research is underway to examine the states of diseases and to explore the causes of the diseases through extensive examination of in vivo proteins. For example, research for determination of proteins that can serve as disease markers, such as cancer marker proteins, is underway.

Furthermore, in recent years, transcriptome analysis has been actively conducted for extensive analysis of RNA expression, as a result of improved DNA chip technology. However, RNA expression profiles do not always agree with the protein expression profiles. The correlation between the two is said to be 50% or less. To achieve the aforementioned purpose, extensive analysis of both protein(s) and RNA is also important. Attempts to elucidate protein functions have been made using a two-dimensional electrophoresis method that has currently been significantly developed, mass spectrometry, and high throughput analysis equivalent to genome analysis such as protein chip analysis.

As described above, methods for analyzing proteins more efficiently are required with the advancement of protein research. Establishment of technology for conveniently and rapidly analyzing a great variety of proteins is important.

Electrophoresis has been broadly employed as a method for analyzing proteins. In proteome research, such electrophoresis is used for comparing protein components contained in normal tissues with those contained in disease tissues (differential display) or for preparing proteins to be used for protein identification, for example.

Electrophoresis requires staining (labeling) proteins for detection. Staining methods are largely classified into two methods.

One method is a pre-staining method that involves labeling a protein before electrophoresis. The other method is a post-staining method that involves labeling a protein after electrophoresis. An example of the former method is an Ettan DIGE method. Examples of the latter method include a Bio-Safe CBB staining method and a Sypro Ruby staining method. The characteristics of these methods are each listed in the following Table 1.

TABLE 1

| Staining method | Binding mode with protein | Pre-staining or post-staining | Operational steps (time required: minute) | Total operation time (minute) | Detection method | Defects |
|---|---|---|---|---|---|---|
| Ettan DIGE | Covalent binding | Pre-staining | Reaction (30) → stop (10) | 40 + α | Fluorescence | After electrophoresis, analysis using a mass spectrometer cannot be performed. |
| Bio-Safe CBB | Non-covalent binding (binding not mediated by SDS) | Post-staining | Immobilization (30) → staining (60) → washing (30) | 120 + α | Visible | Poor detection sensitivity |
| Sypro Ruby | Non-covalent binding (binding not mediated by SDS) | Post-staining | Immobilization (30) → staining (180) → washing (30) | 240 + α | Fluorescence | Good detection sensitivity. However, staining and washing processes require long time (half a day to one day in some cases). |

In the case of the Ettan DIGE method, proteins in a sample are labeled in advance with a fluorescent reagent via covalent binding before electrophoresis. This method requires a short total operation time and has high general versatility, but it is problematic in that a plurality of fluorescent reagents bind to one protein molecule and the number of such fluorescent reagent bound to each protein differs depending on the protein in question. Hence, proteins separated by electrophoresis cannot be subjected to mass spectrometry in proteomic analysis.

In the cases of the Bio-Safe CBB method and the Sypro Ruby method, the post-staining methods, a series of complicated steps such as:
a. immobilization of proteins on gel and removal of SDS;
b. staining of proteins with a fluorescent reagent;
c. washing off of excess fluorescent reagent; and
d. detection
must be performed after completion of electrophoresis. In particular, when steps "a" and "c" are omitted or the operation time is shortened, problems arise, such as proteins being insufficiently stained with a fluorescent reagent and the background fluorescence intensity being increased so as to make it difficult to detect protein spots.

The present inventors have reported a reagent capable of forming a complex with a protein to vary the resulting fluorescence or luminescence, so as to enable rapid and convenient analysis of the protein (JP Patent Application No. 2005-167613).

DISCLOSURE OF THE INVENTION

An object of the present invention is to provide a method for analyzing proteins using electrophoresis, by which problems associated with electrophoresis employed for protein analysis including:
many operational steps and lengthy required time;
poor detection sensitivity;
proteins that cannot be subjected to mass spectrometry after separation; and the like are addressed and rapid and convenient analysis of a great variety of proteins with high sensitivity is made possible.

The present inventors have conducted concentrated studies in order to attain the above objects. As a result, the present inventors have discovered that proteins can be rapidly and conveniently analyzed with high sensitivity by setting a sample in gel for electrophoresis, performing electrophoresis of the sample using a buffer for electrophoresis in which a specific labeling compound is dissolved, and then detecting a complex of the labeling compound and the protein via spectrophotometrical measurement. Thus, the present inventors have completed the present invention.

The present invention includes the following inventions.
(1) A method for analyzing a protein in a sample, comprising setting a sample in a carrier for electrophoresis, performing electrophoresis for the sample using a buffer for electrophoresis in which a labeling compound represented by formula I:

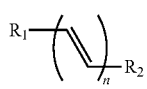

(I)

wherein $R_1$ is an aryl group or a heteroaryl group that may be substituted, $R_2$ is a heterocyclic group that may be substituted, and n is an integer between 1 and 5, is dissolved, and then detecting a complex of the compound of formula I and the protein via spectrophotometrical measurement.
(2) The method according to (1) above, wherein $R_2$ is a group represented by formula II:

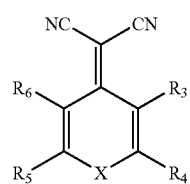

(II)

wherein $R_3$, $R_4$, $R_5$, and $R_6$ are independently from each other selected from the group consisting of a hydrogen atom, a C1-10 alkyl group, a C1-10 alkoxy group, a phenyl group (and such phenyl group may be substituted with one or more groups selected from among an amino group, halogen, and a nitro group), an amino group, a cyano group, a nitro group, a carboxyl group (or a salt, ester, or amide thereof), sulfonic acid (or a salt, ester, or amide thereof), a thiol group, a hydroxy group (or a salt thereof), a C1-10 acyl group, halogen, and sugar; X is an —NR— group (wherein R is hydrogen or a C1-5 alkyl group), an oxygen atom, or a sulfur atom; and any one of $R_3$, $R_4$, $R_5$, and $R_6$ is a bond.
(3) The method according to (1) or (2) above, wherein $R_1$ is a phenyl group, a naphthyl group, a pyridyl group, or a furyl group that may be substituted.

Conventional protein analysis methods using electrophoresis have defects such as poor sensitivity, poor accuracy, complicated operation, and lengthy required time. However, the method of the present invention possesses the following characteristics such that:
a labeling reagent and a protein form a complex via non-covalent binding, so as to enable further mass spectrometric analysis of the protein separated by electrophoresis;
steps and operation can be simplified and operation time can be drastically shortened (particularly, time for staining and time for washing); and
detection sensitivity is good.

Thus, according to the method of the present invention, proteins in a sample can be precisely and conveniently detected within a short time using electrophoresis, qualitatively analyzed, and quantitatively analyzed.

This description includes part or all of the contents as disclosed in the description and/or drawings of Japanese Patent Application No. 2005-304478, which is a priority document of the present application.

PREFERRED EMBODIMENTS OF THE INVENTION

Figure 1:
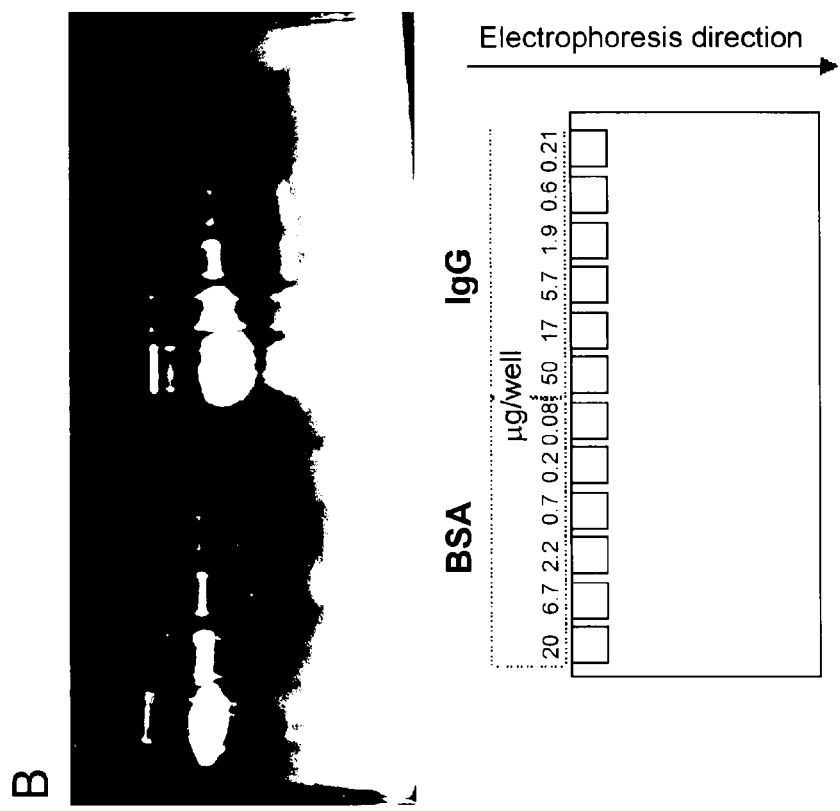
FIG. 1 shows fluorescence observed after electrophoresis performed in Example 4 (labeling reagent at a concentration of 0.5 mg/mL; A: before washing, B: after washing; excitation wavelength of 480 nm; detection wavelength of 530 nm).
Figure 1:
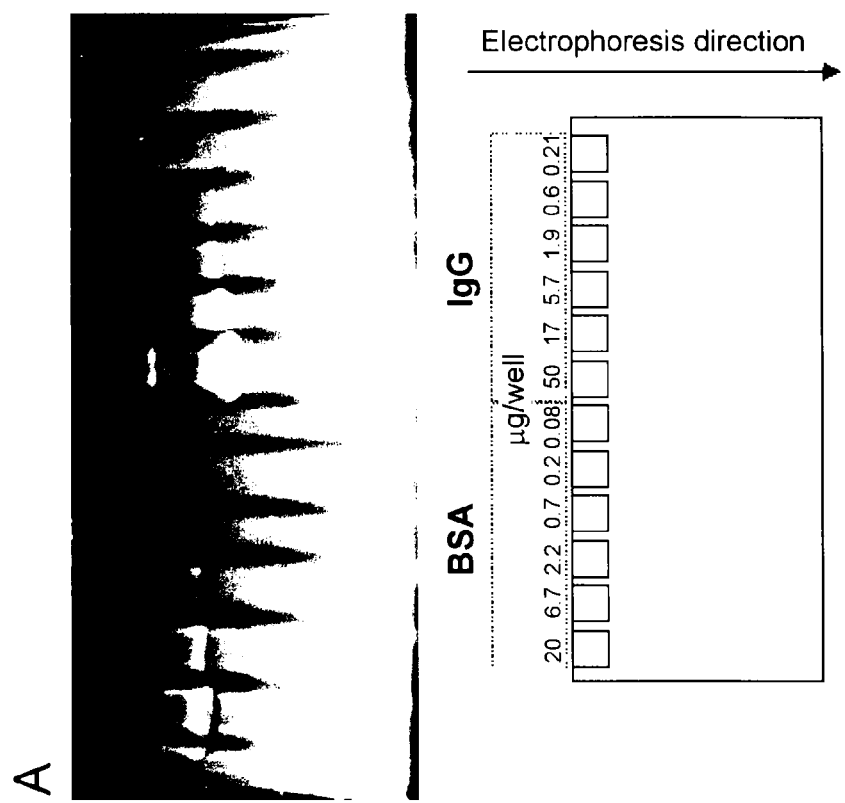

The present invention is a method for analyzing a protein, comprising setting a sample in gel for electrophoresis, performing electrophoresis for the sample using a buffer for electrophoresis in which a labeling compound represented by formula I:

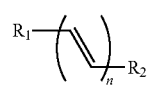

(I)

wherein $R_1$ is an aryl group or a heteroaryl group that may be substituted, $R_2$ is a heterocyclic group that may be substituted, and n is an integer between 1 and 5, is dissolved, and then detecting a complex of the compound of formula I and the protein via spectrophotometrical measurement. In addition, "protein" in the present invention is a concept including "peptide" comprising about dozens of amino acid residues.

According to the method of the present invention, electrophoresis is performed using a labeling reagent for analyzing proteins as disclosed in the previous application (JP Patent Application No. 2005-167613), so that staining (labeling) and separation of proteins are performed simultaneously. To achieve this, a labeling reagent is mixed in advance with a buffer for gel electrophoresis. When electrophoresis is initiated, the labeling reagent infiltrates the gel with electroosmotic flow and then forms a complex (CT complex) with proteins existing in a sample set in the gel. Formation of such complex causes a change in fluorescence, luminescence, or the like of the labeling reagent. Proteins are analyzed by measuring such change with spectroscopical measures (including checking by eye).

Examples of carriers for electrophoresis used in the present invention are not particularly limited, as long as they are generally used as carriers for electrophoresis and include membranes (e.g., a cellulose acetate membrane, a nitrocellulose membrane, and a polyvinylidene difluoride (PVDF) membrane) and gel (e.g., polyacrylamide gel or agarose gel). In the present invention, it is preferable to use gel as a carrier and it is particularly preferable to use SDS-polyacrylamide gel.

The compound represented by formula I is used for labeling (staining) a protein contained in an analytical sample. The compound forms a complex with the protein to show altered fluorescence, luminescence, coloration, absorption wavelength (e.g., absorption in the ultraviolet [UV] region, in the visible region, and in the infrared region) or to generate the same. Compounds that enable detection of such changes using spectroscopical measures (including checking by eye) are preferable.

In formula I, $R_1$ is an aryl group or a heteroaryl group that may be substituted, $R_2$ is a heterocyclic group that may be substituted, and n is an integer between 1 and 5.

Examples of the aryl group include phenyl and a polycyclic aromatic group (e.g., naphthyl, anthryl, and pyrenyl) in which 2 to 4 benzene rings are fused. Furthermore, the heteroaryl group refers to an aryl group containing at least one heteroatom selected from the group consisting of N, O, and S as its ring-forming atom. Such aryl group or heteroaryl group may be an aryl group or heteroaryl group further fused with another aromatic ring or heteroaromatic ring. Specific examples of such aryl group and heteroaryl group include a pyridyl group, a furyl group, a dansyl group, coumarin, benzothiazole, fluorescein, rhodamine, and azobenzene.

The aryl group or the heteroaryl group may be substituted with one or more groups selected from the group consisting of a C1-10 (preferably C1-6) alkyl group, a C1-10 (preferably C1-6) alkoxy group, a phenyl group (and such phenyl group may be substituted with one or more groups selected from among an amino group, halogen, and a nitro group), an amino group, a cyano group, a nitro group, a carboxyl group (or a salt, ester, or amide thereof), sulfonic acid (or a salt, ester, or amide thereof), a thiol group, and a hydroxy group (or a salt thereof), a C1-10 (preferably C1-6) acyl group, halogen, and sugar. The aryl group or the heteroaryl group is preferably substituted with a hydroxy group for imparting of water solubility and electron-donating ability.

The heterocyclic group is preferably a fluorescent group or a chromogenic group (absorption and fluorescence in the ultraviolet [UV] region, those in the visible region, and those in the infrared region can be measured) that has at least one heteroatom as an ring-forming atom and forms a conjugate system the an olefin portion —(CH═CH)n- represented by formula I. Examples of such heterocyclic group include coumarin, benzothiazole, fluorescein, and rhodamine. In the present invention, a group represented by formula II:

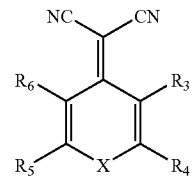

wherein $R_3$, $R_4$, $R_5$, and $R_6$ are independently from each other selected from the group consisting of a hydrogen atom, a C1-10 alkyl group, a C1-10 alkoxy group, a phenyl group (and such phenyl group may be substituted with one or more groups selected from among an amino group, halogen, and a nitro group), an amino group, a cyano group, a nitro group, a carboxyl group (or a salt, ester, or amide thereof), sulfonic acid (or a salt, ester, or amide thereof), a thiol group, and a hydroxy group (or a salt thereof), and a C1-10 acyl group, halogen, and sugar; X is an —NR— group (wherein R is hydrogen or a C1-5 alkyl group), an oxygen atom, or a sulfur atom; and any one of $R_3$, $R_4$, $R_5$, and $R_6$ is a bond, is preferable.

Furthermore, a group represented by the following formula:

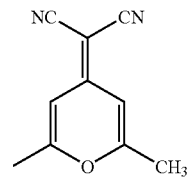

is preferable.

Connection of an alkenyl group and an aromatic group to $R_2$, which serves as a fluorescent group or a chromogenic group, results in an elongated conjugate system and promotes lengthening of fluorescence and coloration wavelengths.

A compound of formula I can be easily synthesized by a known method. For example, a compound of the following formula:

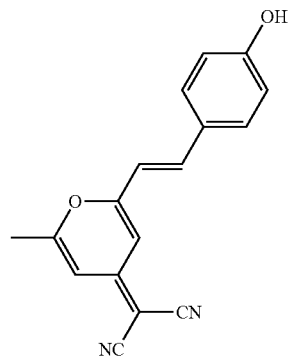

can be produced by reacting 4-hydroxybenzaldehyde with 4-(dicyanomethylene)-2,6-dimethyl-4H-pyran in ethanol in the presence of a nucleotide (e.g., amine such as piperidine).

Next, the procedures of the method of the present invention will be described below. The method of the present invention is the same as a conventional method in that it employs electrophoresis, but is different therefrom in terms of the compound to be used for labeling and in that steps are simplified in the method of the present invention. Schemes are shown below for comparison of the method of the present invention with the conventional method.

TABLE 2

Conventional method

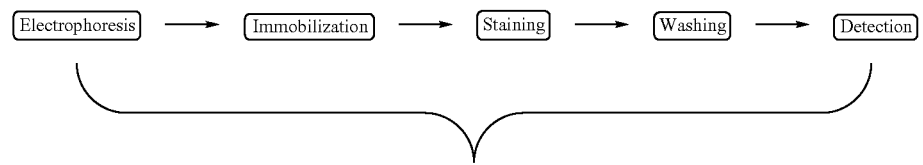

These steps require a time period about 3 hours at the shortest or may take a half a day longer.

The present invention

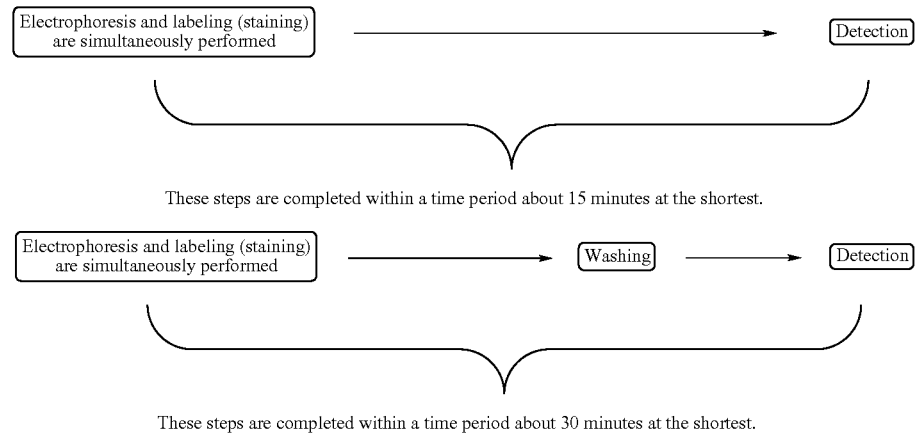

These steps are completed within a time period about 15 minutes at the shortest.

These steps are completed within a time period about 30 minutes at the shortest.

Specifically, the conventional method requires a series of steps (electrophoresis-protein immobilization-staining-washing-detection) before detection of proteins is performed after completion of electrophoresis. However, the method of the present invention requires only short steps (staining-detection of protein) while performing electrophoresis because of the use of the compound of formula I as a labeling reagent, so that the time required for analysis can be drastically shortened.

According to the method of the present invention, first, a sample containing proteins is applied to an electrophoretic carrier. A buffer for electrophoresis may be a generally used buffer. In the present invention, such a buffer in which a compound of formula I is dissolved is used. Subsequently, electrophoresis is performed in a manner similar to that of a general method, thereby fractionating the proteins in the sample.

During electrophoresis, the compound of formula I contained in the buffer forms a charge-transfer complex with the proteins in the sample (that is, the proteins are labeled) through hydrophobic interaction and charge-transfer interaction while migrating with electroosmotic flow. Through the formation of such complex, absorption wavelength, absorption intensity, fluorescence wavelength, fluorescence intensity, and the like unique to the compound of formula I may vary. This variation may be checked by eye as a change in color tone.

After completion of electrophoresis, the carrier (gel) is removed. The carrier may be washed with a lavage solution, if desired. The thus removed carrier is observed by spectroscopical measures (e.g., a fluorometer or an absorptiometer; checking by eye is also included herein) capable of detecting fluorescence, luminescence, coloration, absorption wavelength (e.g., absorption in the ultraviolet [UV] region, the visible region, and the infrared region) and the like. When a reagent by which fluorescence is generated is used, observation is performed using a fluorescence detector. When a reagent by which absorption wavelength is generated in the visible region is used, checking by eye is performed. Thus, protein spots can be easily detected in both cases. As described above, a protein in a sample can be detected or qualitatively analyzed. Moreover, proteins in a sample can also be quantitatively analyzed by measuring the intensity of fluorescence, luminescence, coloration, or the like.

The method of the present invention can also be applied not only to one-dimensional electrophoresis, but also to two-dimensional electrophoresis.

Hereafter, the present invention is described in greater detail with reference to the following examples, although the present invention is not limited to these examples.

EXAMPLE 1

Synthesis of Dye 1

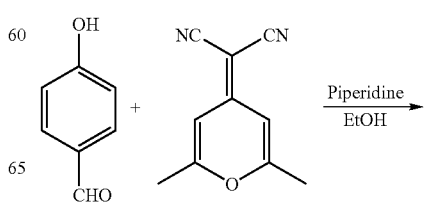

-continued

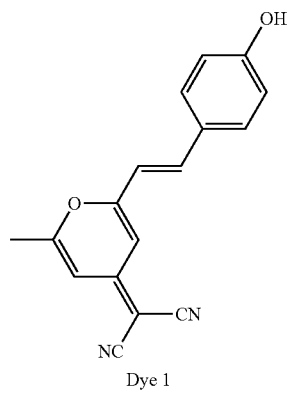

Dye 1

0.70 g of 4-hydroxybenzaldehyde (5.81 mmol), 1.0 g of 4-(dicyanomethylene)-2,6-dimethyl-4H-pyran (5.81 mmol), 0.50 g of piperidine (5.81 mmol), and 50 ml of ethanol were added to a 50-ml three neck flask. The solution was heated to reflux for 12 hours under an Ar stream. After the solvent was distilled away under reduced pressure, the resultant was purified by column chromatography (SiO$_2$, CHCl$_3$: MeOH=10:1 v/v) so that a target compound was obtained. Yield: 30%.

EXAMPLE 2

Synthesis of Dye 2

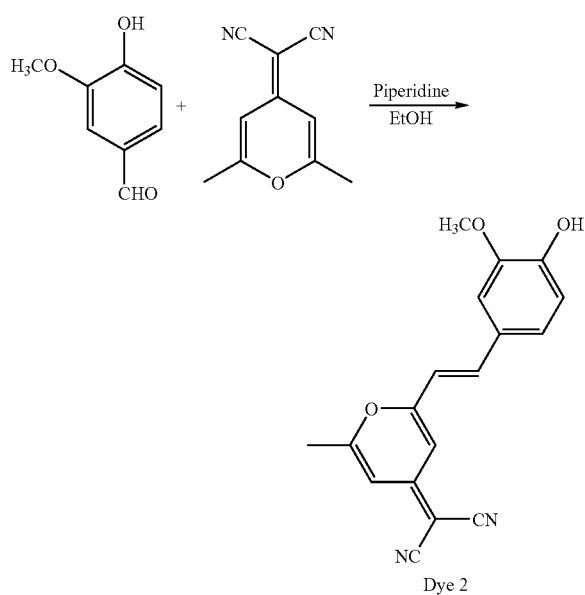

Dye 2

0.70 g of vanillin (5.81 mmol), 1.0 g of 4-(dicyanomethylene)-2,6-dimethyl-4H-pyran (5.81 mmol), 0.50 g of piperidine (5.81 mmol), and 50 ml of ethanol were added to a 50-ml three neck flask. The solution was heated to reflux for 12 hours under an Ar stream. After the solvent was distilled away under reduced pressure, the resultant was purified by column chromatography (SiO$_2$, CHCl$_3$:MeOH=10:1 v/v) so that a target compound was obtained. Yield: 20%.

EXAMPLE 3

Synthesis of Dye 3

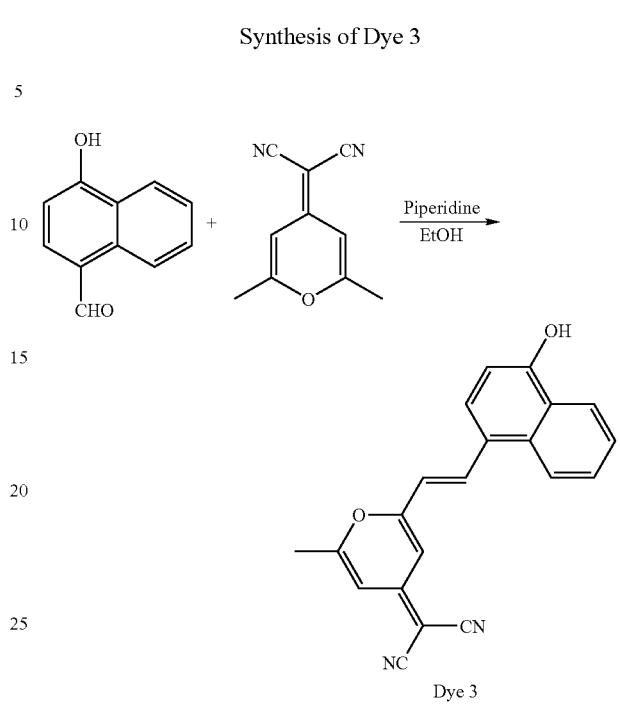

Dye 3

0.70 g of 4-hydroxy-1-naphthaldehyde (5.81 mmol), 1.0 g of 4-(dicyanomethylene)-2,6-dimethyl-4H-pyran (5.81 mmol), 0.50 g of piperidine (5.81 mmol), and 50 ml of ethanol were added to a 50-ml three neck flask. The solution was heated to reflux for 12 hours under an Ar stream. After the solvent was distilled away under reduced pressure, the resultant was purified by column chromatography (SiO$_2$, CHCl$_3$:MeOH=10:1 v/v) so that a target compound was obtained. Yield: 25%.

EXAMPLE 4

Protein Analysis by One-Dimensional Electrophoresis

Dye 3 prepared in Example 3 was used as a labeling reagent. Electrophoresis performed herein was one-dimensional electrophoresis using SDS-polyacrylamide gel as a carrier. Measurement conditions for the one-dimensional electrophoresis are as described below.
<Electrophoresis System>
Sure Blot F1 Gel system: produced by Astellas Pharma Inc.
<Buffer for Electrophoresis>
A stock solution (DMSO solution at a concentration of 500 mg/mL) of dye 3 was diluted with an electrophoresis buffer attached to a Sure Blot F1 Gel system. The thus obtained 0.5 mg/mL, 0.1 mg/mL, and 0.05 mg/mL solutions were used.
<Protein Concentrations in Samples>
[BSA]=0.08 to 20 μg/well and [Sheep IgG]=0.21 to 50 μg/well
<Composition of Lavage Solution>
AcOH:MeOH:H$_2$O=3:10:87 v/v
<Fluorescence Detector>
ProXpress Imaging System (Produced by Perkin-Elmer) and LS400 Scanner (Produced by Tecan)
An electrophoresis buffer (containing dye 3 at a concentration of 0.5 mg/mL) was added to an upper buffer (cathode side). An SDS-PAGE gel to which samples (BSA and IgG) had been applied was set, followed by electrophoresis. After completion of electrophoresis, the gel was removed and then observed using a fluorescence detector (FIG. 1A). Subsequently, the gel was washed for 30 minutes using a lavage solution and then protein spots were observed using the fluorescence detector (FIG. 1B).

Figure 2:
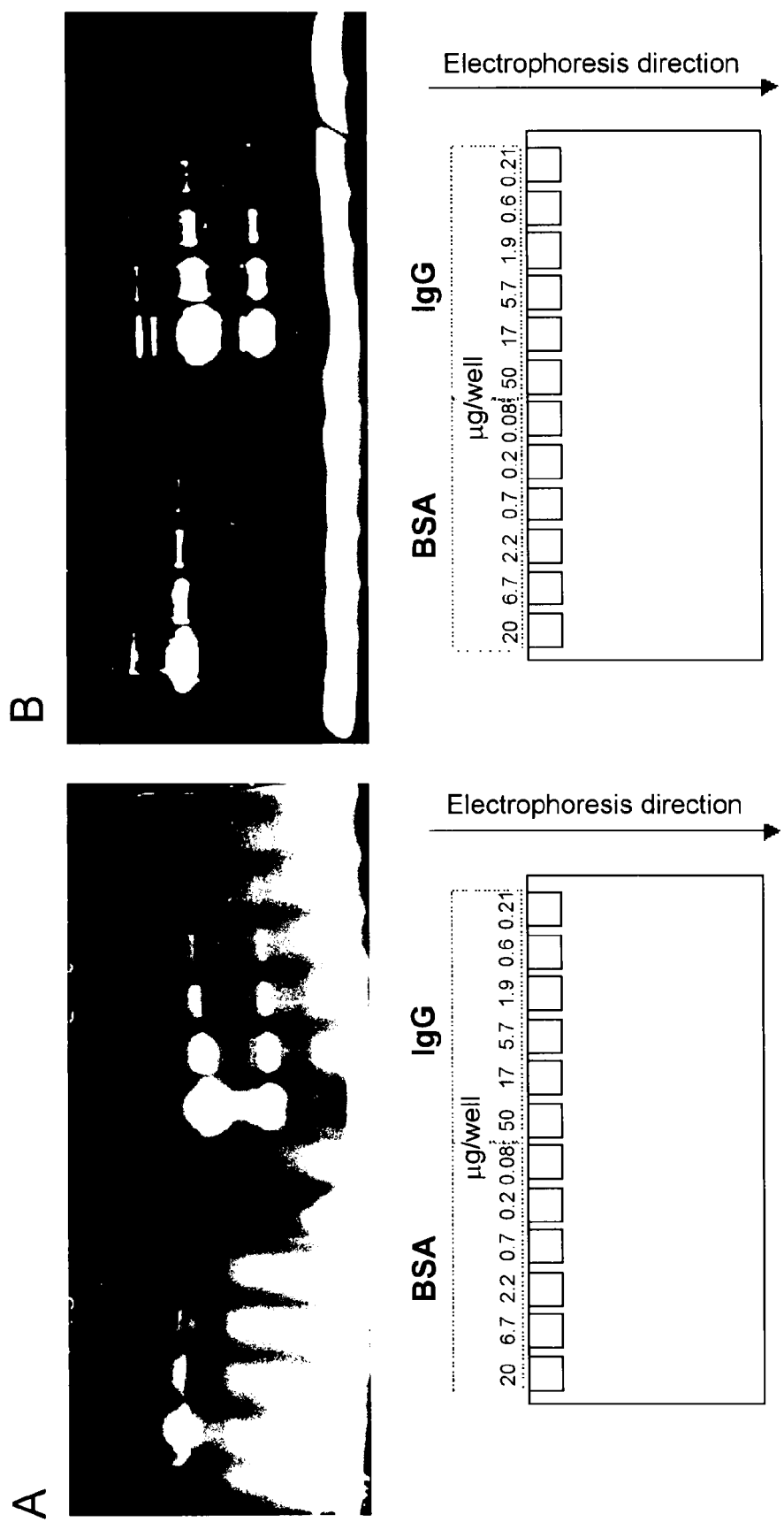
FIG. 2 shows fluorescence observed after electrophoresis performed in Example 4 (labeling reagent at a concentration of 0.1 mg/mL; A: before washing, B: after washing; excitation wavelength of 480 nm; detection wavelength of 530 nm).

Furthermore, electrophoresis was performed similarly using an electrophoresis buffer containing dye 3 at a concentration of 0.1 mg/mL. After completion of electrophoresis, the gel was removed and then observed using a fluorescence detector (FIG. 2A). Subsequently, the gel was washed for 30 minutes using a lavage solution and then protein spots were observed using the fluorescence detector (FIG. 2B).

Protein spots were clearly confirmed in all of these cases. It was understood that proteins had formed complexes with labeling reagents during electrophoresis such that they were altered to generate fluorescence. Moreover, as shown in FIG. 1B and FIG. 2B, the background was reduced via washing of the gel, allowing protein spots to be detected more clearly. Moreover, as shown in FIG. 2A and FIG. 2B, protein spots could also be clearly observed by adjusting the concentration of the labeling reagent in electrophoresis buffer to 0.1 mg/mL.

EXAMPLE 5

Protein Analysis by Two-dimensional Electrophoresis

Dye 3 prepared in Example 3 was used as a labeling reagent. An SDS-polyacrylamide gel carrier was used for two-dimensional electrophoresis. Measurement conditions employed herein are as described below.
<Electrophoresis System>
One-dimensional: Isoelectric focusing; ZOOM IPG runner system (produced by Invitrogen)
Two-dimensional: SDS-PAGE Sure Blot F1 Gel system (produced by Astellas Pharma Inc.)
<Buffer for Electrophoresis>
Stock solutions (DMSO solution at a concentration of 500 mg/mL) of dye 3 were diluted with electrophoresis buffers attached to a Sure Blot F1 Gel system. The thus obtained 0.5 mg/mL, 0.1 mg/mL, and 0.05 mg/mL solutions were used.
<Protein Concentration in Each Sample>
[Mouse Brain Lysate]=40 μg/strip
<Composition of Lavage Solution>
AcOH:MeOH:$H_2O$=3:10:87 v/v
<Fluorescence Detector>
ProXpress imaging system (produced by Perkin-Elmer) and LS400 scanner (produced by Tecan)

Figure 3:
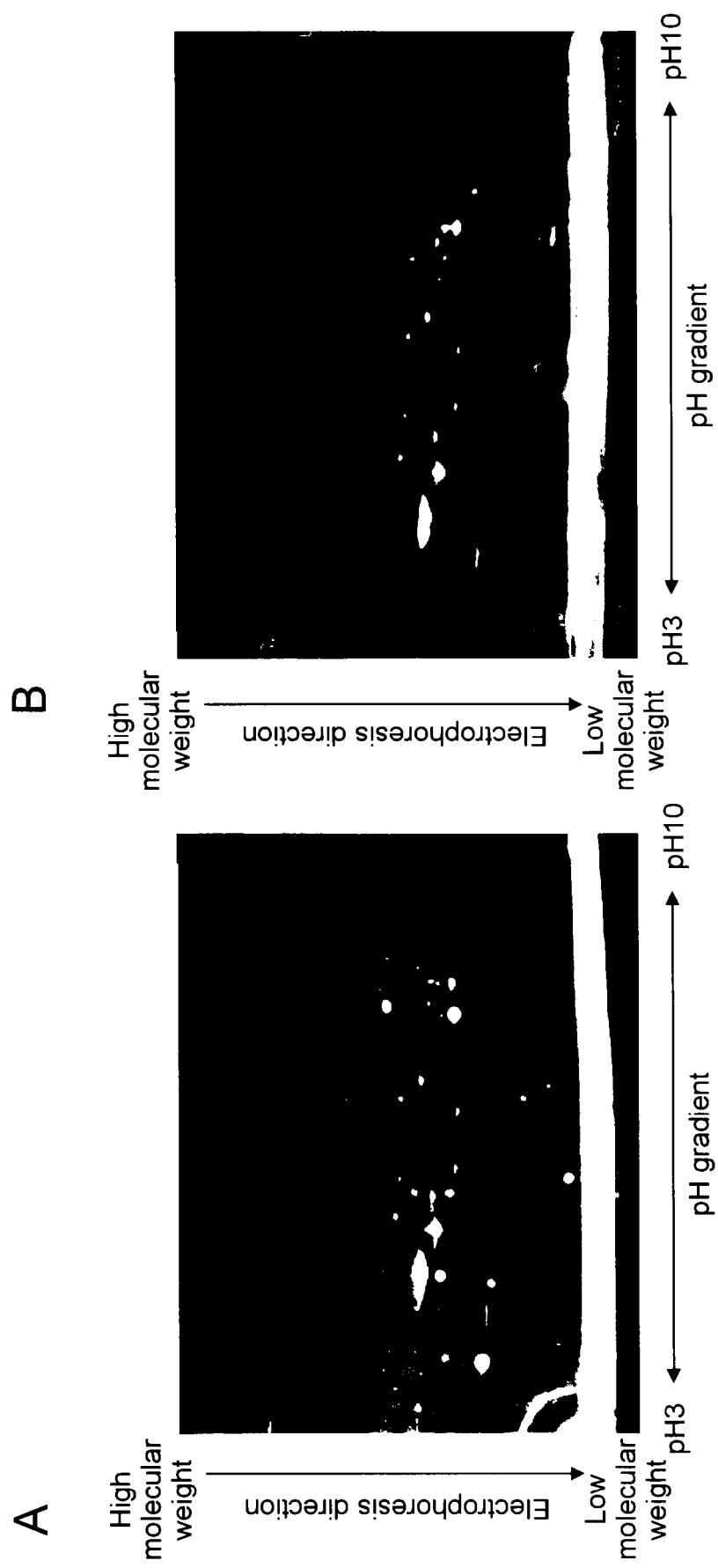
FIG. 3 shows fluorescence observed after two-dimensional electrophoresis performed in Example 5 (labeling reagent at a concentration of 0.1 mg/mL; A: before washing, B: after washing; excitation wavelength of 480 nm; detection wavelength of 530 nm).

The first dimension of two-dimensional electrophoresis was performed by subjecting each sample to isoelectric focusing. Subsequently, an electrophoresis buffer (containing dye 3 at a concentration of 0.5 mg/mL) was added to the upper buffer (cathode side). The sample was applied to an SDS-PAGE gel and then the SDS-PAGE gel was set, so that the second dimension of two-dimensional electrophoresis was performed. After completion of electrophoresis, the gel was removed and then observed using a fluorescence detector (FIG. 3A). Subsequently, the gel was washed for 30 minutes using a lavage solution and then protein spots were observed using the fluorescence detector (FIG. 3B). Protein spots were clearly confirmed in all of these cases. It was understood that proteins had formed complexes with labeling reagents during electrophoresis such that they were altered to generate fluorescence. Moreover, as shown in FIG. 3B, the background was reduced via washing of the gel, allowing protein spots to be detected more clearly.

INDUSTRIAL APPLICABILITY

The method for analyzing proteins of the present invention makes it possible to perform high throughput analysis of a great variety of proteins. Hence, the method of the present invention is useful for extensive and convenient protein analysis with high sensitivity in the fields of biochemistry, medicine, analytical chemistry, proteome research, and the like.

All publications, patents, and patent applications cited herein are incorporated herein by reference in their entirety.

The invention claimed is:

1. A method for analyzing a protein in a sample, comprising setting a sample in a carrier for electrophoresis, performing electrophoresis for the sample in an electrophoresis buffer in which a labeling compound represented by formula I:

wherein $R_1$ is an aryl group or heteroaryl group substituted with a hydroxyl group, $R_2$ is a heterocyclic group that may be substituted, and n is an integer between 1 and 5, is dissolved, and then detecting a complex of the compound of formula I and the protein via spectrophotometrical measurement.

2. The method according to claim 1, wherein $R_2$ is a group represented by formula II:

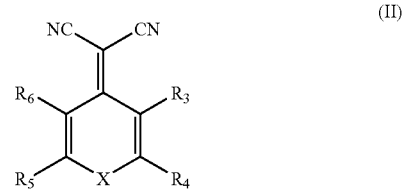

wherein $R_3$, $R_4$, $R_5$, and $R_6$ are independently from each other selected from the group consisting of a hydrogen atom, a C1-10 alkyl group, a C1-10 alkoxy group, a phenyl group (and such phenyl group may be substituted with one or more groups selected from among an amino group, halogen, and a nitro group), an amino group, a cyano group, a nitro group, a carboxyl group (or a salt, ester, or amide thereof), sulfonic acid (or a salt, ester, or amide thereof), a thiol group, a hydroxy group (or a salt thereof), a C1-10 acyl group, halogen, and sugar; X is an —NR— group (wherein R is hydrogen or a C1-5 alkyl group), an oxygen atom, or a sulfur atom; and any one of $R_3$, $R_4$, $R_5$, and $R_6$ is a bond.

3. The method according to claim 1, wherein $R_1$ is a phenyl group substituted with a hydroxyl group.

4. The method according to claim 1, wherein $R_2$ is

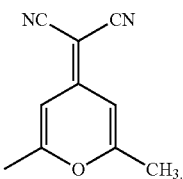

5. A method for analyzing a protein in a sample, comprising setting a sample in a carrier for electrophoresis, performing electrophoresis for the sample in an electrophoresis buffer in which a labeling compound represented by formula I:

(I)

wherein $R_1$ is a polycyclic aromatic group in which 2 to 4 benzene rings are fused;
$R_2$ is a heterocyclic group that may be substituted, and n is an integer between 1 and 5,
is dissolved, and then detecting a complex of the compound of formula I and the protein via spectrophotometrical measurement.

6. The method according to claim 1, wherein the labeling compound is

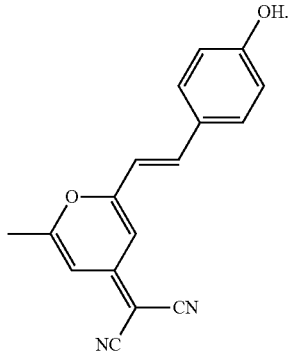

7. A method for analyzing a protein in a sample, comprising setting a sample in a carrier for electrophoresis, performing electrophoresis for the sample in an electrophoresis buffer in which a labeling compound is dissolved, and then detecting a complex of the labeling compound and the protein via spectrophotometrical measurement, wherein the labeling compound is

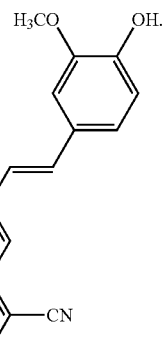

8. The method according to claim 5, wherein the labeling compound is

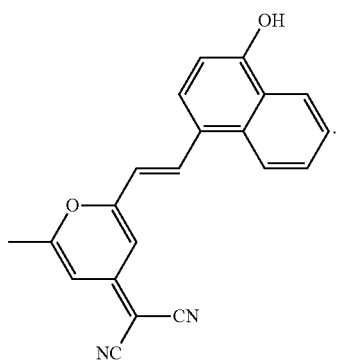

* * * * *